United States Patent

Muntz

[11] Patent Number: 5,873,859
[45] Date of Patent: Feb. 23, 1999

[54] METHOD AND APPARATUS FOR SELF INJECTING MEDICINE

[76] Inventor: Robert L. Muntz, 307 Evans, Aurora, Ill. 60505

[21] Appl. No.: 839,957

[22] Filed: Apr. 24, 1997

[51] Int. Cl.⁶ .................................................. A61M 5/00
[52] U.S. Cl. ............................ 604/207; 141/27; 604/407
[58] Field of Search ................................... 604/207, 208, 604/187, 414, 411, 407; 141/27

[56] References Cited

U.S. PATENT DOCUMENTS

| | | | |
|---|---|---|---|
| 3,875,979 | 4/1975 | Hults | 141/27 |
| 4,252,159 | 2/1981 | Maki | 141/27 |
| 4,434,820 | 3/1984 | Glass | 141/27 |
| 5,487,738 | 1/1996 | Sciulli | 604/187 X |
| 5,620,422 | 4/1997 | Halbich | 604/208 X |

*Primary Examiner*—John D. Yasko

[57] ABSTRACT

A new Method and Apparatus for Self Injecting Medicine for offering a device designed to assist individuals who must give self injections. The inventive device includes a support base, a track, a sub-base, syringe plunger retainer, syringe nose retainer and a medicine vial support. In use, a syringe is inserted and retainably, removably attached with the handle between the first wall and the second wall and the plunger therefore protrudingly extending out a first end of the device and wherein a nose of the syringe is retainably and removably held within a syringe nose retainer by biasedly opposing spring fingers wherein arcuate bottle mating surface engages a periphery of a medicine vial and therefore supports and retains the medicine vial from movement to and aft and rotationally and wherein adjustment of the medicine vial can be accomplished linearly within the sliding track and the medicine vial can therefore be slid to allow a needle of the syringe to protrudingly extend into the medicine vial, therefore allowing removal of liquid medicine by the drawing back of a plunger of the syringe.

9 Claims, 2 Drawing Sheets

METHOD AND APPARATUS FOR SELF INJECTING MEDICINE

BACKGROUND OF THE INVENTION

1. Field of the Invention

The present invention relates to medicine dispensing syringes and more particularly pertains to a new Method and Apparatus for Self Injecting Medicine for offering a device designed to assist individuals who must give self injections.

2. Description of the Prior Art

The use of medicine dispensing syringes is known in the prior art. More specifically, medicine dispensing syringes heretofore devised and utilized are known to consist basically of familiar, expected and obvious structural configurations, notwithstanding the myriad of designs encompassed by the crowded prior art which have been developed for the fulfillment of countless objectives and requirements.

Known prior art medicine dispensing syringes include U.S. Pat. No. 5,356,406; U.S. Pat. No. 4,944,736; U.S. Pat. Des. 347,894; U.S. Pat. No. 4,665,959; U.S. Pat. No. 5,188,620; and U.S. Pat. No. 5,125,921.

While these devices fulfill their respective, particular objectives and requirements, the aforementioned patents do not disclose a new Method and Apparatus for Self Injecting Medicine. The inventive device includes a support base, a track, a sub-base, syringe plunger retainer, syringe nose retainer and a medicine vial support. The inventive device is produced of plastic and measures approximately 8 inches in length and 1 ½ inches in width and includes suction cups on the base to enable the device to be held in place on any flat surface. Positioned at one end of the base is a clip into which the medicine vial would be secured and attached at the opposite end is a stabilizing support into which the syringe is inserted. This holds the syringe and the barrel in a secure position while the syringe is being filled from the vial. The vial is locked in place but can be easily removed when a replacement is necessary. The clip is adjusted to position the hub of the vial in an accessible location to allow the individual to insert the syringe.

In these respects, the Method and Apparatus for Self Injecting Medicine according to the present invention substantially departs from the conventional concepts and designs of the prior art, and in so doing provides an apparatus primarily developed for the purpose of offering a device designed to assist individuals who must give self injections.

SUMMARY OF THE INVENTION

In view of the foregoing disadvantages inherent in the known types of medicine dispensing syringes now present in the prior art, the present invention provides a new Method and Apparatus for Self Injecting Medicine construction wherein the same can be utilized for offering a device designed to assist individuals who must give self injections.

The general purpose of the present invention, which will be described subsequently in greater detail, is to provide a new Method and Apparatus for Self Injecting Medicine apparatus and method which has many of the advantages of the medicine dispensing syringes mentioned heretofore and many novel features that result in a new Method and Apparatus for Self Injecting Medicine which is not anticipated, rendered obvious, suggested, or even implied by any of the prior art medicine dispensing syringes, either alone or in any combination thereof.

To attain this, the present invention generally comprises a support base, a track, a sub-base, syringe plunger retainer, syringe nose retainer and a medicine vial support and by securing the vial in a proper position, the syringe is easier to insert and fill. This therefore reduces the dangers of accidental needle sticks. The device provides the individual with greater control and allows the individual to keep his or her hands free to concentrate on the syringe without the worry of holding both the syringe and the medicine vial. Therefore the individual is better able to draw the correct amount of medication and therefore reduces the likelihood of accidental overdose or of sometimes equally dangerous under medication condition.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Method and Apparatus for Self Injecting Medicine apparatus and method which has many of the advantages of the medicine dispensing syringes mentioned heretofore and many novel features that result in a new Method and Apparatus for Self Injecting Medicine which is not anticipated, rendered obvious, suggested, or even implied by any of the prior art medicine dispensing syringes, either alone or in any combination thereof.

It is another object of the present invention to provide a new Method and Apparatus for Self Injecting Medicine which may be easily and efficiently manufactured and marketed.

It is a further object of the present invention to provide a new Method and Apparatus for Self Injecting Medicine which is of a durable and reliable construction.

An even further object of the present invention is to provide a new Method and Apparatus for Self Injecting Medicine which is susceptible of a low cost of manufacture with regard to both materials and labor, and which accordingly is then susceptible of low prices of sale to the consuming public, thereby making such Method and Apparatus for Self Injecting Medicine economically available to the buying public.

Still yet another object of the present invention is to provide a new Method and Apparatus for Self Injecting Medicine which provides in the apparatuses and methods of the prior art some of the advantages thereof, while simultaneously overcoming some of the disadvantages normally associated therewith.

Still another object of the present invention is to provide a new Method and Apparatus for Self Injecting Medicine for offering a device designed to assist individuals who must give self injections.

Yet another object of the present invention is to provide a new Method and Apparatus for Self Injecting Medicine which includes a support base, a track, a sub-base, syringe plunger retainer, syringe nose retainer and a medicine vial support.

Still yet another object of the present invention is to provide a new Method and Apparatus for Self Injecting Medicine that securely holds a medicine vial in an appropriate position to allow the individual to easily and safely fill a syringe with the medication contained within the vial.

Even still another object of the present invention is to provide a new Method and Apparatus for Self Injecting Medicine that reduces the likelihood of accidental needle sticks by making access easier and more convenient, while reducing the spills and therefore waste of the medicine.

Still yet another object of the present invention is to provide a new Method and Apparatus for Self Injecting Medicine that enables individuals to obtain a more accurate dosage and decrease the likelihood of accidental spills.

Even still another object of the present invention is to provide a new Method and Apparatus for Self Injecting Medicine that is compact and easy to use and secures to any flat surface, including a sink or counter top.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
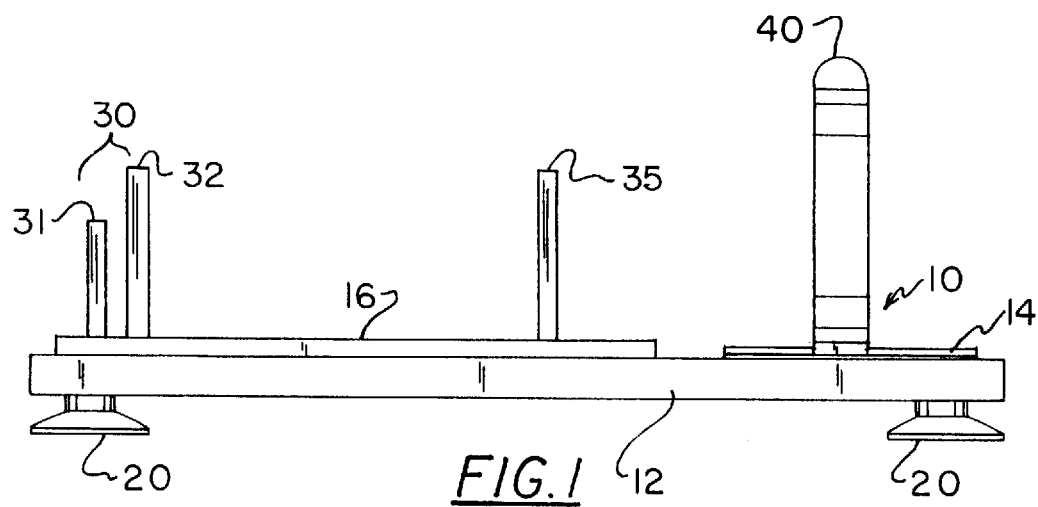
FIG. 1 is a side elevation view of a new Method and Apparatus for Self Injecting Medicine according to the present invention.
Figure 2:
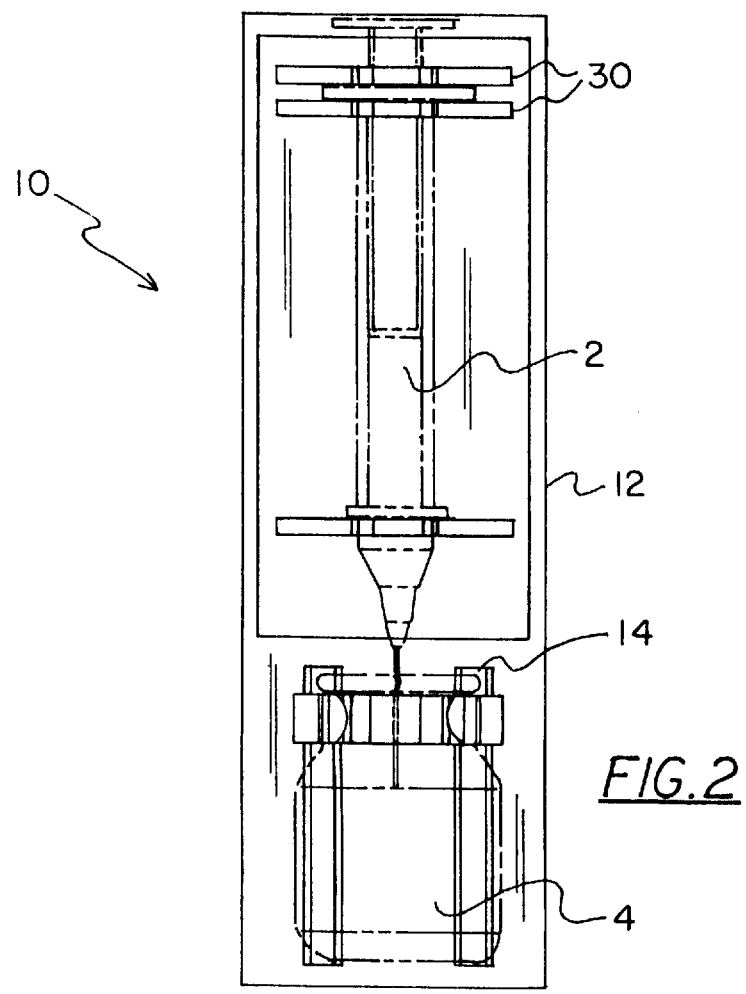
FIG. 2 is a top plan view of the present invention.
Figure 3:
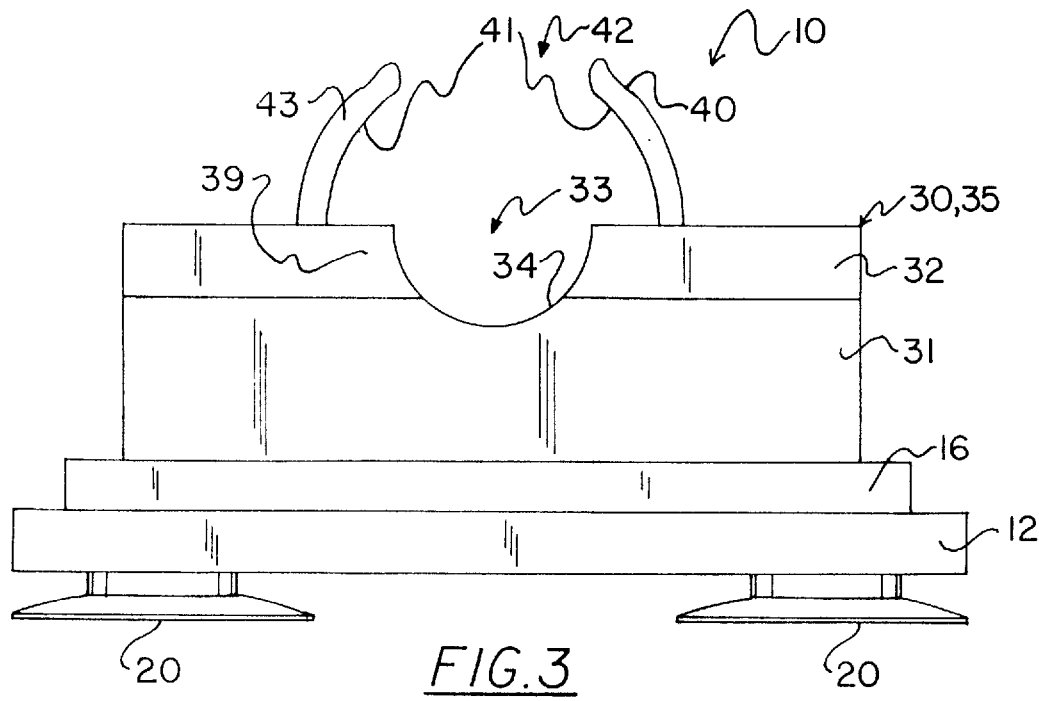
FIG. 3 an end profile view of a syringe end of the present invention.
Figure 4:
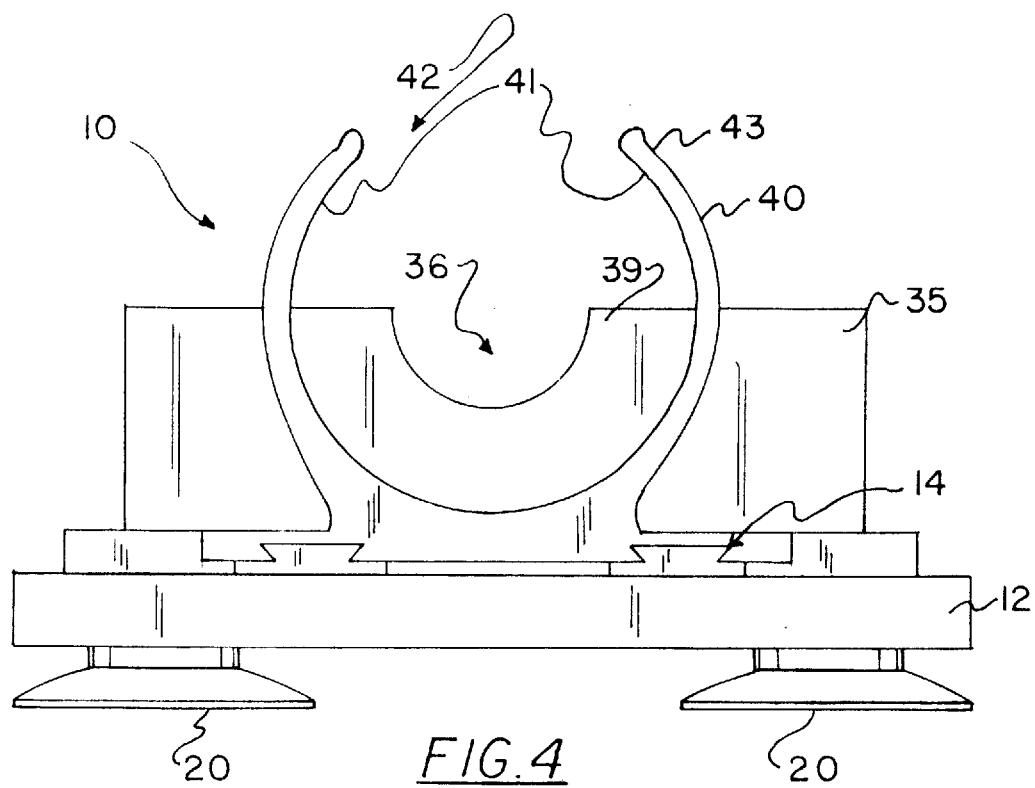
FIG. 4 is an end elevation view of the vial end of the present invention.

With reference now to the drawings, and in particular to FIGS. 1 through 4 thereof, a new Method and Apparatus for Self Injecting Medicine embodying the principles and concepts of the present invention and generally designated by the reference numeral 10 will be described.

More specifically, it will be noted that the Method and Apparatus for Self Injecting Medicine 10 comprises a support base 12, a track 14, a sub-base 16, a syringe plunger retainer 30, a syringe nose retainer 35, and a medicine vial support 40 where the syringe plunger retainer 30 is fixedly attached to the sub-base 16 and the syringe nose retainer 35 is also fixedly attached to the sub-base 16 and wherein the sub-base 16 is fixedly attached to the support base 12 and wherein the medicine vial support 40 is adjustably attached to the tracks 14 which in turn are fixedly attached to the support base 12.

As best illustrated in FIGS. 1 through 4, it can be shown that the support base 12 further comprises suction cups 20 which are attachedly fixed to a bottom of the support base 12 and where there is at least one suction cup 20 or a plurality of suction cups 20.

Additionally, the syringe plunger retainer 30 is comprised of a first wall 31, a second wall 32, a handle aperture 33, an adhering surface 34, a syringe nose retainer 35, a syringe aperture 36, and a resilient spring material 39 where the first wall 31, the second wall 32, and the syringe nose retainer 35 are each fixedly attached orthogonally to an upper side of the sub-base 16 and where the first wall 31 and the second wall 32 each include the handle aperture 33 which in turn is an upward oriented concave arcuate notch and therefore defines the adhering surface 34 which is made into resilient spring material 39 and thereby, the first wall 31 and the second wall 32 further include the adhering surface 34 in each, and where the syringe nose retainer 35 includes the syringe aperture 36 which in turn is an upward oriented concave arcuate notch and therefore defines the adhering surface 34 which is made into resilient spring material 39 and thereby the syringe nose retainer 35 further includes the adhering surface 34 as well.

The handle aperture 33 and the syringe aperture 36 are axially inline and concavely coplanar and therefore the arcuate notches that they define are inline with each other and therefore the adhering surfaces 34 are axially inline and concavely coplanar.

The medicine vial support 40 is comprised of an arcuate bottle mating surface 41, a bottle aperture 42, and at least one spring finger 43 where the spring finger 43, in a current embodiment, is further defined as a pair of concavely shaped arcuate upwardly extending elongations which are orthogonally and integrally joined to a base which forms an upper half of the tracks 14 and where the pair of concavely shaped arcuate upwardly extending elongations further include turned out tips for receiving a bottle diameter of a medicine vial 4 and where an inner side of the pair of concavely shaped arcuate upwardly extending elongations is further defined as the arcuate bottle mating surface 41 and where the pair of concavely shaped arcuate upwardly extending elongations further define two opposing spring biased members that are spaced apart to define a diameter and therefore the bottle aperture 42 which is substantially of a size to mate with a plurality of bottle diameters of various medicine vials 4.

In use, a syringe 2 is inserted and retainably, removably attached with the handle between the first wall 31 and the second wall 32 and the plunger therefore protrudingly extending out a first end of the device and wherein a nose of the syringe is retainably and removably held within a syringe nose retainer 35 by biasedly opposing spring fingers 43 wherein arcuate bottle mating surface 41 engages a periphery of a medicine vial 4 and therefore supports and retains the medicine vial 4 from movement to and aft and rotationally and wherein adjustment of the medicine vial 4 can be accomplished linearly within the sliding track 14 and the medicine vial can therefore be slid to allow a needle of the syringe 2 to protrudingly extend into the medicine vial 4, therefore allowing removal of liquid medicine by the drawing back of a plunger of the syringe 2.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An apparatus for self injecting medicine comprising:

a support base, a track, a sub-base, a syringe plunger retainer, a syringe nose retainer, and a medicine vial support where the syringe plunger retainer is fixedly attached to the sub-base and the syringe nose retainer is also fixedly attached to the sub-base and wherein the sub-base is fixedly attached to the support base and wherein the medicine vial support is adjustably attached to the tracks which in turn are fixedly attached to the support base;

wherein the support base further comprises suction cups which are attachedly fixed to a bottom of the support base and where there is at least one suction cup or a plurality of suction cups; and wherein the syringe plunger retainer is comprised of a first wall, a second wall, a handle aperture, an adhering surface, a syringe nose retainer, a syringe aperture, and a resilient spring material where the first wall, the second wall, and the syringe nose retainer are each fixedly attached orthogonally to an upper side of the sub-base and where the first wall and the second wall each include the handle aperture which in turn is an upward oriented concave arcuate notch and therefore defines the adhering surface which is made into resilient spring material and thereby, the first wall and the second wall further include the adhering surface in each.

2. The apparatus for self injecting medicine of claim 1, wherein the syringe nose retainer includes the syringe aperture which in turn is an upward oriented concave arcuate notch and therefore defines the adhering surface which is made into resilient spring material and thereby the syringe nose retainer further includes the adhering surface.

3. The apparatus for self injecting medicine of claim 2, wherein the handle aperture and the syringe aperture are axially inline and concavely coplanar and therefore the arcuate notches that they define are inline with each other and therefore the adhering surfaces are axially inline and concavely coplanar.

4. The apparatus for self injecting medicine of claim 3, wherein the medicine vial support is comprised of an arcuate bottle mating surface, a bottle aperture, and at least one spring finger where the spring finger is further defined as a pair of concavely shaped arcuate upwardly extending elongations which are orthogonally and integrally joined to a base which forms an upper half of the tracks.

5. The apparatus for self injecting medicine of claim 4, wherein the pair of concavely shaped arcuate upwardly extending elongations further include turned out tips for receiving a bottle diameter of a medicine vial.

6. The apparatus for self injecting medicine of claim 5, wherein an inner side of the pair of concavely shaped arcuate upwardly extending elongations is further defined as the arcuate bottle mating surface.

7. The apparatus for self injecting medicine of claim 6, wherein the pair of concavely shaped arcuate upwardly extending elongations further define two opposing spring biased members that are spaced apart to define a diameter and therefore the bottle aperture which is substantially of a size to mate with a plurality of bottle diameters.

8. An apparatus for filling a syringe of the type having a nose and a flange proximate a plunger, the apparatus comprising:

a base having a first slotted wall and a second slotted wall, said first and second walls extending upwardly from said base and being spaced apart to form a gap between the first and second walls, said gap being adapted to receive the flange of the syringe such that the syringe is prevented from moving horizontally when said gap receives the flange;

a syringe nose retainer extending upwardly from said base, said syringe nose retainer being adapted to receive the nose of the syringe;

a vial support adapted to hold a vial, said vial support being slidably coupled to said base such that said vial support can slide towards and away from the syringe nose retainer such that the syringe can penetrate the vial by sliding the vial towards the syringe.

9. The apparatus of claim 8, further comprising:

a number of suction cups positioned on a bottom surface of said base, said number of suction cups being adapted for securing said base to a surface.

* * * * *